(12) United States Patent
Adams et al.

(10) Patent No.: US 8,589,415 B2
(45) Date of Patent: *Nov. 19, 2013

(54) METHOD AND SYSTEM FOR FILTERING FALSE POSITIVES

(75) Inventors: Norm Adams, Cave Creek, AZ (US); Scott Ellard, Marietta, GA (US); Scott Schumacher, Northridge, CA (US)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 12/687,304

(22) Filed: Jan. 14, 2010

(65) Prior Publication Data

US 2010/0114877 A1      May 6, 2010

Related U.S. Application Data

(63) Continuation of application No. 11/521,946, filed on Sep. 15, 2006, now Pat. No. 7,698,268.

(51) Int. Cl.
*G06F 7/00* (2006.01)
*G07F 17/30* (2006.01)

(52) U.S. Cl.
USPC ........................................................ 707/749

(58) Field of Classification Search
None
See application file for complete search history.

(56) References Cited

U.S. PATENT DOCUMENTS

| | | | |
|---|---|---|---|
| 4,531,186 A | 7/1985 | Knapman | |
| 5,020,019 A | 5/1991 | Ogawa | |
| 5,134,564 A | 7/1992 | Dunn et al. | |
| 5,247,437 A | 9/1993 | Vale et al. | |
| 5,321,833 A | 6/1994 | Chang et al. | |
| 5,323,311 A | 6/1994 | Fukao et al. | |
| 5,333,317 A | 7/1994 | Dann | |
| 5,381,332 A | 1/1995 | Wood | |

(Continued)

FOREIGN PATENT DOCUMENTS

| | | |
|---|---|---|
| JP | 2000348042 | 12/2000 |
| JP | 2001236358 | 8/2001 |

(Continued)

OTHER PUBLICATIONS

Original Paper: "Record Linkage in the National Dose Registry of Canada" by M.E. Fair., pp. S37-S43.

(Continued)

*Primary Examiner* — Jason Liao
(74) *Attorney, Agent, or Firm* — Elissa Wang; Edell, Shapiro & Finnan, LLC

(57) ABSTRACT

Embodiments of systems and methods for reducing false positives during the linking of data records are disclosed herein. Broadly speaking, embodiments of the present invention may be used in the generation of an overall weight from the comparison of various attributes of data records, where the linking of the data records is dependent on the overall weight. More specifically, embodiments of the present invention may calculate a false positive penalty based on a set of results, each of the set of results based on a comparison of an attribute. The false positive penalty may be subtracted from the overall weight generated from the comparison of the attributes of data records to adjust the overall weight. By configuring which attributes of the data records are used as the set of attributes for generating the false positive penalty, and the penalties associated with a particular combination of results for the comparisons of these attributes, the incidence of false positives in the linking of data records may be significantly reduced.

15 Claims, 4 Drawing Sheets

(56) References Cited

U.S. PATENT DOCUMENTS

| | | |
|---|---|---|
| 5,442,782 A | 8/1995 | Malatesta et al. |
| 5,497,486 A | 3/1996 | Stolfo et al. |
| 5,535,322 A | 7/1996 | Hecht |
| 5,535,382 A | 7/1996 | Ogawa |
| 5,537,590 A | 7/1996 | Amado |
| 5,555,409 A | 9/1996 | Leenstra et al. |
| 5,561,794 A | 10/1996 | Fortier |
| 5,583,763 A | 12/1996 | Atcheson et al. |
| 5,600,835 A | 2/1997 | Garland et al. |
| 5,606,690 A | 2/1997 | Hunter et al. |
| 5,615,367 A | 3/1997 | Bennett et al. |
| 5,640,553 A | 6/1997 | Schultz |
| 5,651,108 A | 7/1997 | Cain et al. |
| 5,675,752 A | 10/1997 | Scott et al. |
| 5,675,753 A | 10/1997 | Hansen et al. |
| 5,694,593 A | 12/1997 | Baclawski |
| 5,694,594 A | 12/1997 | Chang |
| 5,710,916 A | 1/1998 | Barbara et al. |
| 5,734,907 A | 3/1998 | Jarossay et al. |
| 5,765,150 A | 6/1998 | Burrows |
| 5,774,661 A | 6/1998 | Chatterjee |
| 5,774,883 A | 6/1998 | Andersen |
| 5,774,887 A | 6/1998 | Wolff et al. |
| 5,778,370 A | 7/1998 | Emerson |
| 5,787,431 A | 7/1998 | Shaughnessy |
| 5,787,470 A | 7/1998 | DeSimone et al. |
| 5,790,173 A | 8/1998 | Strauss |
| 5,796,393 A | 8/1998 | MacNaughton et al. |
| 5,805,702 A | 9/1998 | Curry |
| 5,809,499 A | 9/1998 | Wong et al. |
| 5,819,264 A | 10/1998 | Palmon et al. |
| 5,835,712 A | 11/1998 | DuFresne |
| 5,835,912 A | 11/1998 | Pet |
| 5,848,271 A | 12/1998 | Caruso et al. |
| 5,859,972 A | 1/1999 | Subramaniam et al. |
| 5,862,322 A | 1/1999 | Anglin et al. |
| 5,862,325 A | 1/1999 | Reed et al. |
| 5,878,043 A | 3/1999 | Casey |
| 5,893,074 A | 4/1999 | Hughes et al. |
| 5,893,110 A | 4/1999 | Weber et al. |
| 5,905,496 A | 5/1999 | Lau et al. |
| 5,930,768 A | 7/1999 | Hooban |
| 5,960,411 A | 9/1999 | Hartman et al. |
| 5,963,915 A | 10/1999 | Kirsch |
| 5,987,422 A | 11/1999 | Buzsaki |
| 5,991,758 A | 11/1999 | Ellard |
| 5,999,937 A | 12/1999 | Ellard |
| 6,014,664 A | 1/2000 | Fagin et al. |
| 6,016,489 A | 1/2000 | Cavanaugh et al. |
| 6,018,733 A | 1/2000 | Kirsch et al. |
| 6,018,742 A | 1/2000 | Herbert, III |
| 6,026,433 A | 2/2000 | D'Arlach et al. |
| 6,049,847 A | 4/2000 | Vogt et al. |
| 6,067,549 A | 5/2000 | Smalley et al. |
| 6,069,628 A | 5/2000 | Farry et al. |
| 6,078,325 A | 6/2000 | Jolissaint et al. |
| 6,108,004 A | 8/2000 | Medl |
| 6,134,581 A | 10/2000 | Ismael et al. |
| 6,185,608 B1 | 2/2001 | Hon et al. |
| 6,223,145 B1 | 4/2001 | Hearst |
| 6,269,373 B1 | 7/2001 | Apte et al. |
| 6,297,824 B1 | 10/2001 | Hearst et al. |
| 6,298,478 B1 | 10/2001 | Nally et al. |
| 6,311,190 B1 | 10/2001 | Bayer et al. |
| 6,327,611 B1 | 12/2001 | Everingham |
| 6,330,569 B1 | 12/2001 | Baisley et al. |
| 6,349,325 B1 | 2/2002 | Newcombe et al. |
| 6,356,931 B2 | 3/2002 | Ismael et al. |
| 6,374,241 B1 | 4/2002 | Lamburt et al. |
| 6,385,600 B1 | 5/2002 | McGuinness et al. |
| 6,389,429 B1 | 5/2002 | Kane et al. |
| 6,446,188 B1 | 9/2002 | Henderson et al. |
| 6,449,620 B1 | 9/2002 | Draper |
| 6,457,065 B1 | 9/2002 | Rich et al. |
| 6,460,045 B1 | 10/2002 | Aboulnaga et al. |
| 6,496,793 B1 | 12/2002 | Veditz et al. |
| 6,502,099 B1 | 12/2002 | Rampy et al. |
| 6,510,505 B1 | 1/2003 | Burns et al. |
| 6,523,019 B1 | 2/2003 | Borthwick |
| 6,529,888 B1 | 3/2003 | Heckerman et al. |
| 6,556,983 B1 | 4/2003 | Altschuler et al. |
| 6,557,100 B1 | 4/2003 | Knutson |
| 6,621,505 B1 | 9/2003 | Beauchamp et al. |
| 6,633,878 B1 | 10/2003 | Underwood |
| 6,633,882 B1 | 10/2003 | Fayyad et al. |
| 6,633,992 B1 | 10/2003 | Rosen |
| 6,647,383 B1 | 11/2003 | August et al. |
| 6,662,180 B1 | 12/2003 | Aref et al. |
| 6,687,702 B2 | 2/2004 | Vaitheeswaran et al. |
| 6,704,805 B1 | 3/2004 | Acker et al. |
| 6,718,535 B1 | 4/2004 | Underwood |
| 6,742,003 B2 | 5/2004 | Heckerman et al. |
| 6,757,708 B1 | 6/2004 | Craig et al. |
| 6,795,793 B2 | 9/2004 | Shayegan et al. |
| 6,807,537 B1 | 10/2004 | Thiesson et al. |
| 6,842,761 B2 | 1/2005 | Diamond et al. |
| 6,842,906 B1 | 1/2005 | Bowman-Amuah |
| 6,879,944 B1 | 4/2005 | Tipping et al. |
| 6,907,422 B1 | 6/2005 | Predovic |
| 6,912,549 B2 | 6/2005 | Rotter et al. |
| 6,922,695 B2 | 7/2005 | Skufca et al. |
| 6,957,186 B1 | 10/2005 | Guheen et al. |
| 6,990,636 B2 | 1/2006 | Beauchamp et al. |
| 6,996,565 B2 | 2/2006 | Skufca et al. |
| 7,035,809 B2 | 4/2006 | Miller et al. |
| 7,043,476 B2 | 5/2006 | Robson |
| 7,099,857 B2 | 8/2006 | Lambert |
| 7,143,091 B2 | 11/2006 | Charnock et al. |
| 7,155,427 B1 | 12/2006 | Prothia |
| 7,181,459 B2 | 2/2007 | Grant et al. |
| 7,249,131 B2 | 7/2007 | Skufca et al. |
| 7,330,845 B2 | 2/2008 | Lee et al. |
| 7,487,173 B2 | 2/2009 | Medicke et al. |
| 7,526,486 B2 | 4/2009 | Cushman, II et al. |
| 7,567,962 B2 | 7/2009 | Chakrabarti et al. |
| 7,620,647 B2 | 11/2009 | Stephens et al. |
| 7,627,550 B1 | 12/2009 | Adams et al. |
| 7,685,093 B1 | 3/2010 | Adams et al. |
| 7,698,268 B1 | 4/2010 | Adams et al. |
| 7,788,274 B1 | 8/2010 | Ionescu |
| 8,321,383 B2 | 11/2012 | Schumacher et al. |
| 8,321,393 B2 | 11/2012 | Adams et al. |
| 8,332,366 B2 | 12/2012 | Schumacher et al. |
| 2002/0007284 A1 | 1/2002 | Schurenberg et al. |
| 2002/0073099 A1 | 6/2002 | Gilbert et al. |
| 2002/0080187 A1 | 6/2002 | Lawton |
| 2002/0087599 A1 | 7/2002 | Grant et al. |
| 2002/0095421 A1 | 7/2002 | Koskas |
| 2002/0099694 A1 | 7/2002 | Diamond et al. |
| 2002/0152422 A1 | 10/2002 | Sharma et al. |
| 2002/0156917 A1 | 10/2002 | Nye |
| 2002/0178360 A1 | 11/2002 | Wenocur et al. |
| 2003/0004770 A1 | 1/2003 | Miller et al. |
| 2003/0004771 A1 | 1/2003 | Yaung |
| 2003/0018652 A1 | 1/2003 | Heckerman et al. |
| 2003/0023773 A1 | 1/2003 | Lee et al. |
| 2003/0051063 A1 | 3/2003 | Skufca et al. |
| 2003/0065826 A1 | 4/2003 | Skufca et al. |
| 2003/0065827 A1 | 4/2003 | Skufca et al. |
| 2003/0105825 A1 | 6/2003 | Kring et al. |
| 2003/0120630 A1 | 6/2003 | Tunkelang |
| 2003/0145002 A1 | 7/2003 | Kleinberger et al. |
| 2003/0158850 A1 | 8/2003 | Lawrence et al. |
| 2003/0174179 A1 | 9/2003 | Suermondt et al. |
| 2003/0182101 A1 | 9/2003 | Lambert |
| 2003/0195836 A1 | 10/2003 | Hayes et al. |
| 2003/0195889 A1 | 10/2003 | Yao et al. |
| 2003/0195890 A1 | 10/2003 | Oommen |
| 2003/0220858 A1 | 11/2003 | Lam et al. |
| 2003/0227487 A1 | 12/2003 | Hugh |
| 2004/0107189 A1 | 6/2004 | Burdick et al. |
| 2004/0107205 A1 | 6/2004 | Burdick et al. |
| 2004/0122790 A1 | 6/2004 | Walker et al. |
| 2004/0143477 A1 | 7/2004 | Wolff |

(56) References Cited

U.S. PATENT DOCUMENTS

| | | |
|---|---|---|
| 2004/0143508 A1 | 7/2004 | Bohn et al. |
| 2004/0181526 A1 | 9/2004 | Burdick et al. |
| 2004/0181554 A1 | 9/2004 | Heckerman et al. |
| 2004/0220926 A1 | 11/2004 | Lamkin et al. |
| 2004/0260694 A1 | 12/2004 | Chaudhuri et al. |
| 2005/0004895 A1 | 1/2005 | Schurenberg et al. |
| 2005/0015381 A1 | 1/2005 | Clifford et al. |
| 2005/0015675 A1 | 1/2005 | Kolawa et al. |
| 2005/0050068 A1 | 3/2005 | Vaschillo et al. |
| 2005/0055345 A1 | 3/2005 | Ripley |
| 2005/0060286 A1 | 3/2005 | Hansen et al. |
| 2005/0071194 A1 | 3/2005 | Bormann et al. |
| 2005/0075917 A1 | 4/2005 | Flores et al. |
| 2005/0114369 A1 | 5/2005 | Gould et al. |
| 2005/0149522 A1 | 7/2005 | Cookson et al. |
| 2005/0154615 A1 | 7/2005 | Rotter et al. |
| 2005/0210007 A1 | 9/2005 | Beres et al. |
| 2005/0228808 A1 | 10/2005 | Mamou et al. |
| 2005/0240392 A1 | 10/2005 | Munro et al. |
| 2005/0256740 A1 | 11/2005 | Kohan et al. |
| 2005/0256882 A1 | 11/2005 | Able et al. |
| 2005/0273452 A1 | 12/2005 | Molloy et al. |
| 2006/0053151 A1 | 3/2006 | Gardner et al. |
| 2006/0053172 A1 | 3/2006 | Gardner et al. |
| 2006/0053173 A1 | 3/2006 | Gardner et al. |
| 2006/0053382 A1 | 3/2006 | Gardner et al. |
| 2006/0064429 A1 | 3/2006 | Yao |
| 2006/0074832 A1 | 4/2006 | Gardner et al. |
| 2006/0074836 A1 | 4/2006 | Gardner et al. |
| 2006/0080312 A1 | 4/2006 | Friedlander et al. |
| 2006/0116983 A1 | 6/2006 | Dettinger et al. |
| 2006/0117032 A1 | 6/2006 | Dettinger et al. |
| 2006/0129605 A1 | 6/2006 | Doshi |
| 2006/0129971 A1 | 6/2006 | Rojer |
| 2006/0136205 A1 | 6/2006 | Song |
| 2006/0161522 A1 | 7/2006 | Dettinger et al. |
| 2006/0167896 A1 | 7/2006 | Kapur et al. |
| 2006/0179050 A1 | 8/2006 | Giang et al. |
| 2006/0190445 A1 | 8/2006 | Risberg et al. |
| 2006/0195560 A1 | 8/2006 | Newport |
| 2006/0265400 A1 | 11/2006 | Fain et al. |
| 2006/0271401 A1 | 11/2006 | Lassetter et al. |
| 2006/0271549 A1 | 11/2006 | Rayback et al. |
| 2006/0287890 A1 | 12/2006 | Stead et al. |
| 2007/0005567 A1 | 1/2007 | Hermansen et al. |
| 2007/0016450 A1 | 1/2007 | Bhora et al. |
| 2007/0055647 A1 | 3/2007 | Mullins et al. |
| 2007/0067285 A1 | 3/2007 | Blume et al. |
| 2007/0073678 A1 | 3/2007 | Scott et al. |
| 2007/0073745 A1 | 3/2007 | Scott et al. |
| 2007/0094060 A1 | 4/2007 | Apps et al. |
| 2007/0150279 A1 | 6/2007 | Gandhi et al. |
| 2007/0192715 A1 | 8/2007 | Kataria et al. |
| 2007/0198481 A1 | 8/2007 | Hogue et al. |
| 2007/0198600 A1 | 8/2007 | Betz |
| 2007/0214129 A1 | 9/2007 | Ture et al. |
| 2007/0214179 A1 | 9/2007 | Hoang |
| 2007/0217676 A1 | 9/2007 | Grauman et al. |
| 2007/0250487 A1 | 10/2007 | Reuther |
| 2007/0260492 A1 | 11/2007 | Feied et al. |
| 2007/0276844 A1 | 11/2007 | Segal et al. |
| 2007/0276858 A1 | 11/2007 | Cushman et al. |
| 2007/0299697 A1 | 12/2007 | Friedlander et al. |
| 2007/0299842 A1 | 12/2007 | Morris et al. |
| 2008/0005106 A1 | 1/2008 | Schumacher et al. |
| 2008/0016218 A1 | 1/2008 | Jones et al. |
| 2008/0069132 A1 | 3/2008 | Ellard et al. |
| 2008/0120432 A1 | 5/2008 | Lamoureux et al. |
| 2008/0126160 A1 | 5/2008 | Takuechi et al. |
| 2008/0243832 A1 | 10/2008 | Adams et al. |
| 2008/0243885 A1 | 10/2008 | Harger et al. |
| 2008/0244008 A1 | 10/2008 | Wilkinson et al. |
| 2008/0276221 A1 | 11/2008 | Lev et al. |
| 2009/0089317 A1 | 4/2009 | Ford et al. |
| 2009/0089332 A1 | 4/2009 | Harger et al. |
| 2009/0089630 A1 | 4/2009 | Goldenberg et al. |
| 2009/0198686 A1 | 8/2009 | Cushman, II et al. |
| 2010/0114877 A1 | 5/2010 | Adams et al. |
| 2010/0174725 A1 | 7/2010 | Adams et al. |
| 2010/0175024 A1 | 7/2010 | Schumacher et al. |
| 2011/0010214 A1 | 1/2011 | Carruth |
| 2011/0010346 A1 | 1/2011 | Goldenberg et al. |
| 2011/0010401 A1 | 1/2011 | Adams et al. |
| 2011/0010728 A1 | 1/2011 | Goldenberg et al. |
| 2011/0047044 A1* | 2/2011 | Wright et al. ............... 705/26.35 |
| 2011/0191349 A1 | 8/2011 | Ford et al. |

FOREIGN PATENT DOCUMENTS

| | | |
|---|---|---|
| JP | 2005063332 | 3/2005 |
| JP | 2006163941 | 6/2006 |
| JP | 2006277413 | 10/2006 |
| WO | 9855947 A1 | 12/1998 |
| WO | 0159586 | 8/2001 |
| WO | 0159586 A2 | 8/2001 |
| WO | 0175679 A1 | 10/2001 |
| WO | 03021485 | 3/2003 |
| WO | 2004023297 A1 | 3/2004 |
| WO | 2004023311 A1 | 3/2004 |
| WO | 2004023345 A1 | 3/2004 |
| WO | 2009042931 A1 | 4/2009 |
| WO | 2009042941 A1 | 4/2009 |

OTHER PUBLICATIONS

Office Action issued in U.S. Appl. No. 11/521,946 mailed May 14, 2008, 10 pgs.

Hamming Distance, HTML. Wikipedia.org, Available: http://en.wikipedia.org/wiki/Hamming_distance (as of May 8, 2008).

Office Action issued in U.S. Appl. No. 11/521,946 mailed Dec. 9, 2008, 10 pgs.

Office Action issued in U.S. Appl. No. 11/521,946 mailed May 13, 2009, 12 pgs.

Fruend et al., Statistical Methods, 1993, Academic Press Inc., United Kingdom Edition, pp. 112-117.

International Preliminary Report on Patentability, PCT/US2008/58404, Mar. 21, 2011, 4 pages.

European Search Report/EP07795659.7, Apr. 15, 2011, 7 pages.

International Search Report and Written Opinion, for PCT/US2007/012073, Mailed Jul. 23, 2008, 12 pages.

International Search Report and Written Opinion issued in PCT/US2007/013049, mailed Jun. 13, 2008.

Oracle Data Hubs: "The Emperor Has No Clothes?", Feb. 21, 2005, Google.com, pp. 1-9.

IEEE, no matched results, Jun. 30, 2009, p. 1.

IEEE No matched Results, 1 Page, Sep. 11, 2009.

Office Action issued in U.S. Appl. No. 11/522,223 dated Aug. 20, 2008, 16 pgs.

Office Action issued in U.S. Appl. No. 11/522,223 dated Feb. 5, 2009, Adams, 17 pages.

Notice of Allowance issued for U.S. Appl. No. 11/522,223, dated Sep. 17, 2009, 20 pages.

De Rose, et al. "Building Structured Web Community Portals: A Top-Down, Compositional, and Incremental Approach", VDLB, ACM, pp. 399-410, Sep. 2007.

Microsoft Dictionary, "normalize", at p. 20, Fifth Edition, Microsoft Corp., downloaded from http://proquest.safaribooksonline.com/0735614954 on Sep. 8, 2008.

Office Action issued in U.S. Appl. No. 11/521,928 dated Apr. 1, 2009, 22 pages.

Office Action issued in U.S. Appl. No. 11/521,928 dated Sep. 16, 2008, 14 pages.

Notice of Allowance issued for U.S. Appl. No. 11/521,928, dated Sep. 18, 2009, 20 pages.

Gopalan Suresh Raj, Modeling Using Session and Entity Beans, Dec. 1998, Web Cornucopia, pp. 1-15.

Scott W. Ambler, Overcoming Data Design Challenges, Aug. 2001, pp. 1-3.

XML, Java, and the future of the Web, Bosak, J., Sun Microsystems, Mar. 10, 1997, pp. 1-9.

(56) References Cited

OTHER PUBLICATIONS

Integrated Document and Workflow Management applied to Offer Processing a Machine Tool Company, Stefan Morschheuser, et al., Dept. of Information Systems I, COOCS '95 Milpitas CA, ACM 0-89791-706-5/95, p. 106-115, 1995.
International Search Report mailed on Jul. 19, 2006, for PCT/IL2005/000784 (6 pages).
Merriam-Webster dictionary defines "member" as "individuals", 2008.
Waddington, D., "Does it signal convergence of operational and analytic MDM?" retrieved from the internet:<URL: http://www.intelligententerprise.com>, 2 pages, Aug. 2006.
International Search Report mailed on Oct. 10, 2008, for PCT Application No. PCT/US07/20311 (10 pp).
International Search Report and Written Opinion issued in PCT/US07/89211, mailing date of Jun. 20, 2008.
International Search Report and Written Opinion for PCT/US08/58404, dated Aug. 15, 2008.
International Search Report and Written Opinion mailed on Dec. 3, 2008 for International Patent Application No. PCT/US2008/077985.
Gu, Lifang, et al., "Record Linkage: Current Practice and Future Directions," CSIRO Mathematical and Informational Sciences, 2003, pp. 1-32.
O'Hara-Schettino, et al., "Dynamic Navigation in Multiple View Software Specifications and Designs," Journal of Systems and Software, vol. 41, Issue 2, May 1998, pp. 93-103.
International Search Report and Written Opinion mailed on Oct. 10, 2008 for PCT Application No. PCT/US08/68979.
International Search Report and Written Opinion mailed on Dec. 2, 2008 for PCT/US2008/077970.
International Search Report and Written Opinion mailed on Aug. 28, 2008 for Application No. PCT/US2008/58665, 7 pgs.
C.C. Gotlieb, Oral Interviews with C.C. Gotlieb, Apr. 1992, May 1992, ACM, pp. 1-72.
Google.com, no match results, Jun. 30, 2009, p. 1.
Supplementary European Search Report for EP 07 79 5659 dated May 18, 2010, 5 pages.
European Communication for EP 98928878 (PCT/US9811438) dated Mar. 10, 2008.
European Communication for EP 98928878 (PCT/US9811438) dated Jun. 26, 2006.
Gill, "OX-LINK: The Oxford Medical Record Linkage System", Internet Citation, 1997.
Newcombe et al., "The Use of Names for Linking Personal Records", Journal of the American Statistical Association, vol. 87, Dec. 1, 1992, pp. 335-349.
Ohgaya, Ryosuke et al., "Conceptual Fuzzy Sets-, NAFIPS 2002, Jun. 27-29, 2002, pp. 274-279.Based Navigation System for Yahoo!".
Xue, Gui-Rong et al., "Reinforcing Web-Object Categorization Through Interrelationships", Data Mining and Knowledge Discover, vol. 12, Apr. 4, 2006, pp. 229-248.
Jason Woods, et al., "Baja Identity Hub Configuration Process", Publicly available on Apr. 2, 2009, Version 1.3.
Initiate Systems, Inc.. "Refining the Auto-Link Threshold Based Upon Scored Sample", Publicly available on Apr. 2, 2009; memorandum.
Initiate Systems, Inc. "Introduction", "False-Positive Rate (Auto-Link Threshold)", Publicly available on Apr. 2, 2009; memorandum.
Jason Woods, "Workbench 8.0 Bucket Analysis Tools", Publicly available on Apr. 2, 2009.
"Parsing" Publicly available on Oct. 2, 2008.
Initiate, "Business Scenario: Multi-Lingual Algorithm and Hub," Publicly available on Apr. 2, 2009.
Initiate, "Business Scenario: Multi-Lingual & Many-To-Many Entity Solutions", Publicly available on Apr. 2, 2009.
Initiate, "Relationships-MLH", presentation; Publicly available on Sep. 28, 2007.
Initiate, "Multi-Lingual Hub Support via Memtype Expansion", Publicly available on Apr. 2, 2009.
Initiate Systems, Inc. "Multi-Language Hubs", memorandum; Publicly available on Apr. 2, 2009.
Initiate, "Business Scenario: Support for Members in Multiple Entities", Publicly available on Oct. 2, 2008.
Initiate, "Group Entities", Publicly available on Mar. 30, 2007.
Jim Cushman, MIO 0.5: MIO As a Source; Initiate; Publicly available on Oct. 2, 2008.
Initiate, "Provider Registry Functionality", Publicly available on Oct. 2, 2008.
Edward Seabolt, "Requirement Specification Feature #NNNN Multiple Entity Relationship", Version 0.1- Draft; Publicly available on Oct. 2, 2008.
Initiate, "Aruba Training Engine Callouts", presentation; Publicly available on Mar. 30, 2007.
Initiate, "Business Scenario: Callout to Third Party System", Publicly available on Oct. 2, 2008.
John Dorney, "Requirement Specification Feature #NNNN Conditional Governance", Version 1.0- Draft; Publicly available on Oct. 2, 2008.
Initiate, Release Content Specification, Identity Hub Release 6.1, RCS Version 1.0; Publicly available on Sep. 16, 2005.
Initiate, "Initiate Identity Hub™ Manager User Manual", Release 6.1; Publicly available on Sep. 16, 2005.
End User Training CMT; CIO Maintenance Tool (CMT) Training Doc; Publicly available on Sep. 29, 2006.
"Hierarchy Viewer—OGT 3.0t", Publicly available on Sep. 25, 2008.
"Building and Searching the OGT", Publicly available on Sep. 29, 2006.
Sean Stephens, "Requirement Specification B2B Web Client Architecture", Version 0.1- Draft; Publicly available on Sep. 25, 2008.
"As of: OGT 2.0", Publicly available on Sep. 29, 2006.
Initiate, "Java SDK Self-Training Guide", Release 7.0; Publicly available on Mar. 24, 2006.
Initiate, "Memtype Expansion Detailed Design", Publicly available on Apr. 2, 2009.
Adami, Giordano et al., "Clustering Documents in a Web Directory", WIDM '03, New Orleans, LA, Nov. 7-8, 2003, pp. 66-73.
Chen, Hao et al., "Bringing Order to the Web: Automatically Categorizing Search Results", CHI 2000, CHI Letters, vol. 2, Issue 1, Apr. 1-6, 2000, pp. 145-152.
"Implementation Defined Segments—Exhibit A", Publicly available on Mar. 20, 2008.
Initiate, "Implementation Defined Segments—Gap Analysis", Publicly available on Mar. 20, 2008.
"Supporting Hierarchies", Publicly available on Nov. 29, 2007.
Xue, Gui-Rong et al., "Implicit Link Analysis for Small Web Search", SIGIR '03, Toronto, Canada, Jul. 28-Aug. 1, 2003, pp. 56-63.
Liu, Fang et al., "Personalized Web Search for iMproving Retrieval Effectiveness", IEEE Transactions on Knowledge and Data Engineering vol. 16, No. 1, Jan. 2004, pp. 28-40.
Anyanwu, Kemafor et al. "SemRank: Ranking complex Relationship Search Results on the Semantic Web", WWW 2005, Chiba, Japan May 10-14, 2005, pp. 117-127.
International Preliminary Report and Patentability issued in PCT/US2007/013049, mailed Dec. 17, 2008.
Office Action issued in U.S. Appl. No. 11/809,792, mailed Aug. 21, 2009, 14 pages.
International Preliminary Report on Patentability Under Chapter 1 for PCT Application No. PCT/US2008/058665, issued Sep. 29, 2009, mailed Oct. 8, 2009, 6 pgs.
Marthe E. Fair et al., "Tutorial on Record Linkage Slides Presentation" Chapter 12, pp. 457-479 Apr. 1997.
European Communication for EP 98928878 (PCT/US9811438) 5 pages, dated Feb. 16, 2006.
European Communication for EP 07795659 (PCT/US2007013049) 6 pages, dated May 27, 2010.
Emdad Ahmed, "A Survey on Bioinformatics Data and Service Integration Using Ontology and Declaration Workflow Query Language", Department of Computer Science, Wayne State University, USA, Mar. 15, 2007, pp. 1-67.
International Preliminary Report on Patentability, PCT/US2007/89211, Apr. 30, 2012, 6 pages.
European Search Report/EP07795108.5, May 29, 2012, 6 pages.

(56) References Cited

OTHER PUBLICATIONS

Chinese Office Action and Translation, App. No. 200880117086.9, Jul. 3, 2013, 10 pages.
European Search Report/EP08833215.0, Jul. 25, 2013, 7 pages.
Elfeky et al., "TAILOR: A Record Linkage Toolbox", IEEE Comp. SOC., vol. Conf. 18, Feb. 26, 2002, pp. 17-28.
Baxter et al., "A Comparison of Fast Blocking Methods for Record Linkage", 2003, pp. 1-6.
Bilenko et al., "Adaptive Blocking: Learning to Scale Up Record Linkage", ICDM '06, Dec. 1, 2006, pp. 87-96.

* cited by examiner

| DIM 1 INDEX | NAME RESULT | GENDER RESULT |
|---|---|---|
| 0 | MISSING | MISSING |
| 1 | EXACT | MISSING |
| 2 | PARTIAL | MISSING |
| 3 | DISAGREE | MISSING |
| 4 | MISSING | AGREE |
| 5 | EXACT | AGREE |
| 6 | PARTIAL | AGREE |
| 7 | DISAGREE | AGREE |
| 8 | MISSING | DISAGREE |
| 9 | EXACT | DISAGREE |
| 10 | PARTIAL | DISAGREE |
| 11 | DISAGREE | DISAGREE |

| | NAME | GENDER | SSN | DOB | BIRTH YEAR DIFF. | BIRTH DATE EDIT DIST |
|---|---|---|---|---|---|---|
| FIRST PERMUTATION | PARTIAL | DISAGREE | | | | |
| SECOND PERMUTATION | | DISAGREE | | DISAGREE | | |
| THIRD PERMUTATION | | DISAGREE | DISAGREE | | | |
| FOURTH AND FIFTH PERMUTATIONS | DISAGREE OR PARTIAL | | | DISAGREE | | |
| FIFTH AND SIXTH PERMUTATIONS | DISAGREE OR PARTIAL | | DISAGREE | | | |
| SEVENTH PERMUTATION | | | | | >15 YEARS | >1 |
| EIGHTH PERMUTATION | | | DISAGREE | DISAGREE | | |

*FIG. 6*

METHOD AND SYSTEM FOR FILTERING FALSE POSITIVES

CROSS-REFERENCE TO RELATED APPLICATION

This application is a continuation of, and claims a benefit of priority under 35 U.S.C. 120 of the filing date of U.S. patent application Ser. No. 11/521,946 by inventors Norm Adams et al. entitled "Method and System for Filtering False Positives" filed on Sep. 15, 2006, the entire contents of which are hereby expressly incorporated by reference for all purposes.

TECHNICAL FIELD OF THE INVENTION

This invention relates generally to associating data records, and in particular to identifying data records that may contain information about the same entity such that these data records may be associated. Even more particularly, this invention relates to the statistical identification of data records for association.

BACKGROUND OF THE INVENTION

In today's day and age, the vast majority of businesses retain extensive amounts of data regarding various aspects of their operations, such as inventories, customers, products, etc. Data about entities, such as people, products, parts or anything else may be stored in digital format in a data store such as a computer database. These computer databases permit the data about an entity to be accessed rapidly and permit the data to be cross-referenced to other relevant pieces of data about the same entity. The databases also permit a person to query the database to find data records pertaining to a particular entity, such that data records from various data stores pertaining to the same entity may be associated with one another.

A data store, however, has several limitations which may limit the ability to find the correct data about an entity within the data store. The actual data within the data store is only as accurate as the person who entered the data, or an original data source. Thus, a mistake in the entry of the data into the data store may cause a search for data about an entity in the database to miss relevant data about the entity because, for example, a last name of a person was misspelled or a social security number was entered incorrectly, etc. A whole host of these types of problems may be imagined: two separate record for an entity that already has a record within the database may be created such that several data records may contain information about the same entity, but, for example, the names or identification numbers contained in the two data records may be different so that it may be difficult to associate the data records referring to the same entity with one other.

For a business that operates one or more data stores containing a large number of data records, the ability to locate relevant information about a particular entity within and among the respective databases is very important, but not easily obtained. Once again, any mistake in the entry of data (including without limitation the creation of more than one data record for the same entity) at any information source may cause relevant data to be missed when the data for a particular entity is searched for in the database. In addition, in cases involving multiple information sources, each of the information sources may have slightly different data syntax or formats which may further complicate the process of finding data among the databases. An example of the need to properly identify an entity referred to in a data record and to locate all data records relating to an entity in the health care field is one in which a number of different hospitals associated with a particular health care organization may have one or more information sources containing information about their patient, and a health care organization collects the information from each of the hospitals into a master database. It is necessary to link data records from all of the information sources pertaining to the same patient to enable searching for information for a particular patient in all of the hospital records.

There are several problems which limit the ability to find all of the relevant data about an entity in such a database. Multiple data records may exist for a particular entity as a result of separate data records received from one or more information sources, which leads to a problem that can be called data fragmentation. In the case of data fragmentation, a query of the master database may not retrieve all of the relevant information about a particular entity. In addition, as described above, the query may miss some relevant information about an entity due to a typographical error made during data entry, which leads to the problem of data inaccessibility. In addition, a large database may contain data records which appear to be identical, such as a plurality of records for people with the last name of Smith and the first name of Jim. A query of the database will retrieve all of these data records and a person who made the query to the database may often choose, at random, one of the data records retrieved which may be the wrong data record. The person may not often typically attempt to determine which of the records is appropriate. This can lead to the data records for the wrong entity being retrieved even when the correct data records are available. These problems limit the ability to locate the information for a particular entity within the database.

To reduce the amount of data that must be reviewed, and prevent the user from picking the wrong data record, it is also desirable to identify and associate data records from the various information sources that may contain information about the same entity. There are conventional systems that locate duplicate data records within a database and delete those duplicate data records, but these systems may only locate data records which are substantially identical to each other. Thus, these conventional systems cannot determine if two data records, with, for example, slightly different last names, nevertheless contain information about the same entity. In addition, these conventional systems do not attempt to index data records from a plurality of different information sources, locate data records within the one or more information sources containing information about the same entity, and link those data records together. Consequently, it would be desirable to be able to associate data records from a plurality of information sources which pertain to the same entity, despite discrepancies between attributes of these data records.

No matter the system utilized to identify and associate data records, however, certain conditions may arise with respect to associating these data records. More specifically, there will almost certainly be cases where data records which should be associated are not (known as false negative) and cases where data records are associated when they do not refer to the same entity (known as a false positive). In certain areas, these conditions may be relatively innocuous, the false negatives and false positives are easily dealt with and no harm may arise. In highly critical areas such as health care industries, however, these conditions may have the potential to cause great harm. This is particularly true for false positives. Mistakenly associating data records which refer to distinct entities may have large ramifications when it comes to the application of medical care and pharmaceuticals.

Thus, there is a need for system and methods for comparing attributes of data records and linking these data records which is operable to filter these linked data records for false positives, and it is to this end that embodiments of the present invention are directed.

SUMMARY OF THE INVENTION

Embodiments of systems and methods for reducing false positives during the linking of data records are disclosed herein. Broadly speaking, embodiments of the present invention may be used in the generation of an overall weight from the comparison of various attributes of data records, where the linking of the data records is dependent on the overall weight. More specifically, embodiments of the present invention may provide a set of code (e.g., a computer program product comprising a set of computer instructions stored on a computer readable medium and executable or translatable by a computer processor) translatable to calculate a false positive penalty based on a set of results, each of the set of results based on a comparison of an attribute. The false positive penalty may be subtracted from the overall weight generated from the comparison of the attributes of data records to adjust the overall weight. By configuring which attributes of the data records are used as the set of attributes for generating the false positive penalty, and the penalties associated with a particular combination of results for the comparisons of these attributes, the incidence of false positives in the linking of data records may be significantly reduced.

In one embodiment, a comparison between attributes from two data records yields a set of results which are, in turn, used to generate a false positive penalty. The overall weight which was determined for the two data records may then be adjusted using this false positive penalty.

In some embodiments, the set of results to utilize in determining a false positive penalty may be configured.

In other embodiments, the attributes utilized to generate the false positive penalty may be the attributes used to determine the overall weight for the two records, or a subset thereof.

In still other embodiments, the false positive penalty to be utilized in conjunction with any particular set of results may be configured.

Embodiments of the present invention may provide the technical advantage of more effective linking of data records through the reduction of the incidences of false positives when linking these data records. More specifically, embodiments of the present invention may prove effective at reducing the incidences of false positives when linking data records pertaining to people, especially when these data records undergoing comparison and linking may comprise members of the same family or the same name.

Other technical advantages of embodiments of the present invention include an almost endless degree of configurability and flexibility. In other words, the attributes, results, other parameters utilized in the determination of the false positive penalty to impose (if any) and the values for false positive penalties themselves may be configurable such that embodiments of the present invention may be fined tuned according to a wide variety of variables.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. Note that the features illustrated in the drawings are not necessarily drawn to scale.

FIG. 6 depicts one embodiment of various permutations for a set of results which may cause a false positive penalty to be imposed.

DETAILED DESCRIPTION

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. Skilled artisans should understand, however, that the detailed description and the specific examples, while disclosing preferred embodiments of the invention, are given by way of illustration only and not by way of limitation. Various substitutions, modifications, additions or rearrangements within the scope of the underlying inventive concept(s) will become apparent to those skilled in the art after reading this disclosure.

Reference is now made in detail to the exemplary embodiments of the invention, examples of which are illustrated in the accompanying drawings. Wherever possible, the same reference numbers will be used throughout the drawings to refer to the same or like parts (elements).

Figure 1:
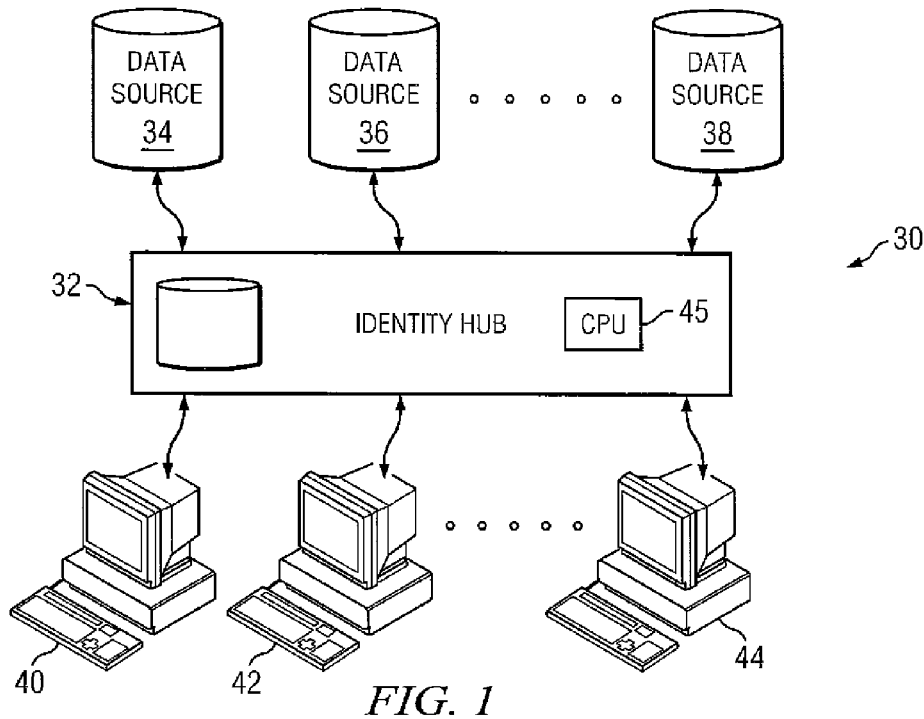
FIG. 1 depicts one embodiment of an example infrastructure.

Before turning to embodiments of the present invention, a general description of an example infrastructure or context which may be helpful in explaining these various embodiments will be described. A block diagram of one embodiment of just such an example infrastructure is described in FIG. 1. FIG. 1 is a block diagram illustrating one embodiment of an entity processing system 30 in accordance with embodiments of the invention. The entity processing system 30 may include an identity hub 32 that processes, updates or stores data pertaining to data records about one or more entities from one or more data sources 34, 36, 38 and responds to commands or queries from a plurality of operators 40, 42, 44, where the operators may be either users or information systems. The identity hub 32 may operate with data records from a single information source or, as shown, data records from multiple information sources. The entities tracked using the identity hub 32 may include for example, patients in a hospital, participants in a health care system, parts in a warehouse or any other entity that may have data records and information contained in data records associated with it. The identity hub 32 may be one or more computer systems with a central processing unit 45 executing computer readable instructions (e.g. a software application) that performs the function of the identity hub 32. The identity hub 32 may also be implemented using hardware circuitry.

As shown, the identity hub 32 may receive data records from the data sources 34, 36, 38 as well as write corrected data back into the information sources 34, 36, 38. The corrected data communicated to the data sources 34, 36, 38 may include information that was correct, but has changed, information about fixing information in a data record or information about links between data records.

In addition, one of the operators 40, 42, 44 may transmit a query to the identity hub 32 and receive a response to the query back from the identity hub 32. The one or more data sources 34, 36, 38 may be, for example, different databases that possibly have data records about the same entities. For example, in the health care field, each information source 34, 36, 38 may be associated with a particular hospital in a health care organization and the health care organization may use the identity hub 32 to relate the data records associated with the plurality of hospitals so that a data record for a patient in Los Angeles may be located when that same patient is on vacation and enters a hospital in New York. The identity hub 32 may be located at a central location and the data sources 34, 36, 38 and users 40, 42, 44 may be located remotely from the identity hub 32 and may be connected to the identity hub 32 by, for example, a communications link, such as the Internet or any other type communications network, such as a wide area network, intranet, wireless network, leased network, etc.

The identity hub 32 may have its own database that stores complete data records in the identity hub, or alternatively, the identity hub may also only contain sufficient data to identify a data record (e.g., an address in a particular data source 34, 36, 38) or any portion of the data fields that comprise a complete data record so that the identity hub 32 can retrieve the entire data record from the data source 34, 36, 38 when needed. The identity hub 32 may link data records together containing information about the same entity utilizing an entity identifier or an associative database separate from actual data records. Thus, the identity hub 32 may maintain links between data records in one or more data sources 34, 36, 38, but does not necessarily maintain a single uniform data record for an entity.

More specifically, the identity hub may link data records in data sources 34, 36, 38 by comparing a data record (received from an operator, or from a data source 34, 36, 38) with other data records in data sources 34, 36, 38 to identify data records which should be linked together. This identification process may entail a comparison of one or more of the attributes of the data records with like attributes of the other data records. For example, a name attribute associated with one record may be compared with the name of other data records, social security number may be compared with the social security number of another record, etc. In this manner, data records which should be linked may be identified.

It will be apparent to those of ordinary skill in the art, that both the data sources 34, 36, 38 and the operators 40, 42, 44 may be affiliated with similar or different organizations or owners. For example, data source 34 may be affiliated with a hospital in Los Angeles run by one health care network, while data source 36 may be affiliated with a hospital in New York run by another health care network. Thus, the data records of each of data sources may be of a different format.

Figure 2A:
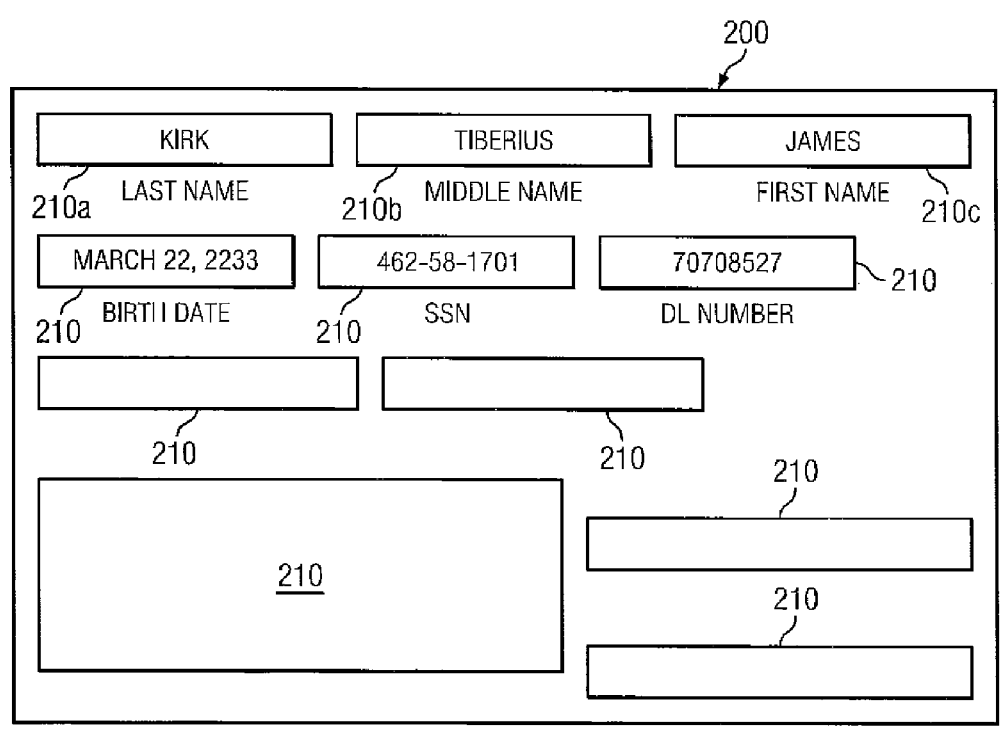
FIGS. 2A and 2B depict a representation of two embodiments of data records.
Figure 2B:
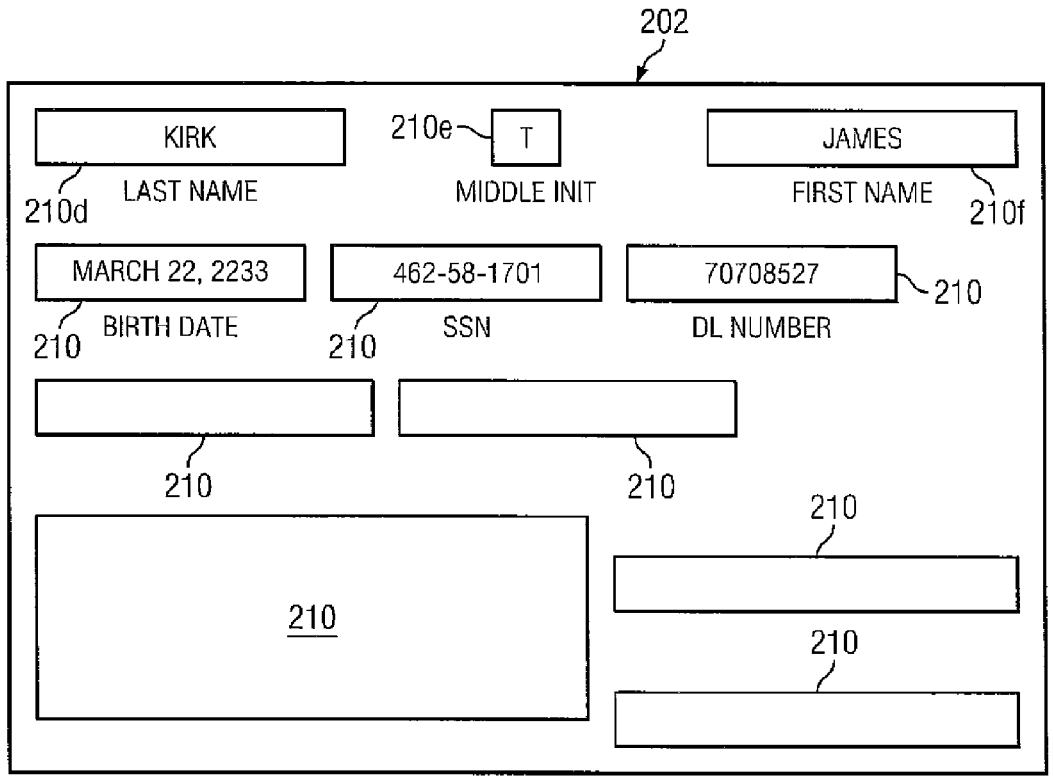

This may be illustrated more clearly with reference to FIGS. 2A and 2B, depicting two embodiments of example data records. Each of these data records 200, 202 has a set of fields 210 corresponding to a set of attributes of each of the data records. For example, one of the attributes of each of the records 200 may be a name, another attribute may be a social security number, birth date, gender, etc. It will be apparent that an attribute may comprise multiple fields 210 of a data record 200, 202, for example, the name attribute of data record 200 may comprise fields 210*a*, 210*b* and 210*c*, the last, middle and first name fields, respectively.

Notice, however, that each of the records may have a different format, for example data record 202 may have a filed for the attribute of driver's license number, while data record 200 may have no such field. Similarly, like attributes may have different formats as well. For example, name fields 210*a*, 210*b*, 210*c* in record 200 may accept the entry of a full first, last and middle name, while name fields 210*d*, 210*e*, 210*f* in record 202 may be designed for full first and last names, but only allow the entry of a middle initial.

As may be imagined, discrepancies such as this may be problematic when comparing two or more data records (e.g. attributes of data records) to identify data records which should be linked. Complicating the linking of data records, information pertaining to the same entity may be incorrectly entered into a data record, or may change in one data record pertaining to the entity but not in another data record, etc.

Figure 3:
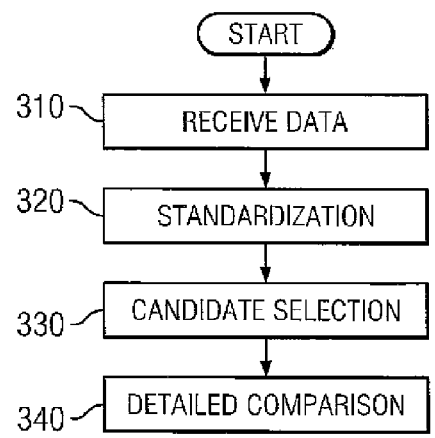
FIG. 3 depicts a flow diagram for one embodiment of comparing data records.

To deal with these possibilities, a system may be utilized which compares the various attributes of data records according to statistical algorithms to determine if data records refer to identical entities and hence, should be linked. To aid in an understanding of the systems and methods of the present invention it will be helpful to present an example embodiment of a methodology for identifying records pertaining to the same entity which may utilize these systems and methods. FIG. 3 depicts one such embodiment. A set of data records for comparison may be given for evaluation at step 310. These data records may include, for example, one or more new data records to compare to a set of existing data records (which may already exist in, for example, data sources 34, 36, 38 or which may be provided as well). At step 320 the data records for comparison may be standardized.

This standardization may comprise the standardization of attributes of a data record into a standard format, such that subsequent comparisons between like attributes of different data records may be performed according to this standard format. It will be apparent that each of the attributes of the data records to be compared may be standardized according to a different format, a different set of semantics or lexicon, etc.

Once the attributes of the data records to be compared have been standardized at step 320, a set of candidates may be selected to compare to the new data record at step 330. This candidate selection process may comprise a comparison of one or more attributes of the new data records to the existing data records to determine which of the existing new data records are similar enough to the new data records to entail further comparison. These candidates may then undergo a more detailed comparison to the new records where a set of attributes are compared between the records to determine if an existing data record should be linked or associated with the new data record. This more detailed comparison may entail comparing each of the set of attributes of one record (e.g. an existing record) to the corresponding attribute in the other record (e.g. the new record) to generate a weight for that attribute. The weights for the set of attributes may then be summed to generate an overall weight which can then be compared to a threshold to determine if the two records should be linked.

In some cases, however, data records which do not represent the same entity may be mistakenly linked. These false positives may occur for a variety of reasons. For example, family members may share a variety of characteristics which, in turn may lead to data records for different members of the same family being incorrectly linked (e.g. it may be incorrectly determined that these data records refer to the same person, and thus the data records linked). Typically, methods for reducing the occurrence of false positives take one or more attributes of the data records being compared and use a fixed penalty if there is a mismatch between any corresponding attribute in their respective data records (e.g. a mismatch penalty is imposed if there is a mismatch between the names in each data records. Because of this, these prior solutions were severely limited in both the combinations of attributes which could be utilized in filtering for false positives, and the final weight penalties that could be imposed for specific combinations of the results of the comparisons of these attributes. Consequently, it would be desirable to implement a false positive filter (e.g. algorithm) to help reduce the likelihood of incorrectly linking data record which associated with different entities, which can be configured to use various attributes which may be used in the linking of records and which may impose differing penalties based on different combinations of results for the evaluation of these attributes.

To that end, attention is now directed to systems and methods for reducing false positives during the linking of data records. Broadly speaking, embodiments of the present invention may be used in the generation of an overall weight from the comparison of various attributes of data records, where the linking of the data records is dependent on the overall weight. More specifically, embodiments of the present invention may calculate a false positive penalty based on a set of results each of the set of results based on a comparison of an attribute. The false positive penalty may be subtracted from the overall weight generated from the comparison of the attributes of data records to adjust the overall weight. By configuring which attributes of the data records are used as the set of attributes for generating the false positive penalty, and the penalties associated with a particular combination of results for the comparisons of these attributes, the incidence of false positives in the linking of data records may be significantly reduced.

Figures 4, 5:
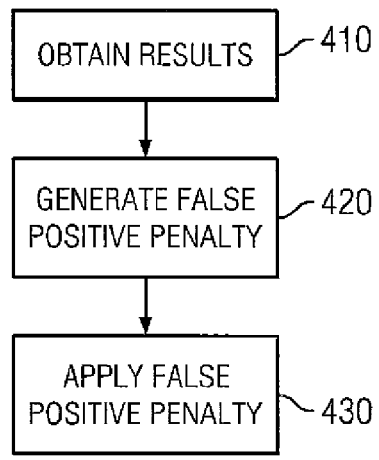
FIG. 4 depicts a flow diagram for one embodiment of determining a false positive penalty.
FIG. 5 depicts a table of values for index values corresponding to one embodiment of the present invention.

Turning now to FIG. 4, a flow diagram for one such embodiment of a method for generating a false positive penalty from the results of the comparisons of each of a set of attributes is depicted. More specifically, one or more attributes of a data record are compared with the corresponding attributes in another data records to generate a weight (e.g. step 340 of FIG. 3), data from the comparison of each of a set of these attributes may be obtained at step 410 (e.g. results), the combination of the results of these comparisons may then be used to generate a false positive penalty at step 420, after which the overall weight may be adjusted according to this false positive penalty at step 430. While embodiments of the present invention will be described in conjunction with a specific set of attributes, it will be understood that embodiments of the invention may be configurable to utilize any set or subset of attributes of data records or results corresponding to the comparison of these attributes, and that the specific penalties associated with any combination of these results may likewise be configurable and different penalties may be assigned for differing combinations results, a single penalty may be assigned for all combinations of results, a single penalty may be assigned for some, but not all, combinations of results, etc.

At step 410, then, the data resulting from the comparisons of a set of attributes may be obtained. The set of attributes or results utilized may be configured to include any set of attributes of the data records being compared, while the data resulting from the comparisons of the attributes may be configured to include the results of the comparison of the attributes or any tokens of the attributes, intermediary results used in the comparisons of attributes or the results of the comparisons of attributes obtained may be generated from comparisons of the attributes or parts of the attributes which were not used in the generation of an overall weight for the two data records.

In one embodiment, the set of attributes utilized may include name, gender, birth date and SSN. The results from the comparison of these attributes may be a name comparison which results in four values for the name comparison "equal"—where all the tokens of the names from each data record match exactly, "partial" if there is one or more initial or nickname/phonetic matches (as depicted in U.S. patent application Ser. No. 11/521,928 titled "Method and System For Comparing Attributes Such as Business Names" by Norm Adams et al. filed on Sep. 15, 2006, and U.S. patent application Ser. No. 11/522,223 entitled "Method and System For Comparing Attributes Such as Personal Names" by Norm Adams et al. and filed on Sep. 15, 2006, both of which are hereby fully incorporated herein by reference), between tokens of either of the names from either attribute and no mismatched between tokens, "different"—there is at least one token mismatch between the two names of the data records and "missing"—where one of the data records is missing name data or no comparison between name attributes was conducted during generation of a weight. It will be apparent that a numerical value may be assigned designating each of the results above.

Similarly, the results of a comparison of the values for the gender attribute of the two data record may be utilized with the three possible results being "agree", "disagree" or "missing"—where at least one of the data records does not have gender data or no comparison of the gender attributes was conducted during the generation of a weight. The results of comparisons of the values for the date of birth attribute of the two data record may also be utilized. One comparison may be the edit distance between the two dates of birth of the data records (e.g. a value of 1 for an edit distance of 1, value of 2 for edit distance of 2, etc.), while another comparison may be the difference in birth year. The difference in birth year may be represented by values, where 0 indicated that birth year data is missing or has not been compared, a value indicates a difference in birth year between 0 and 4 years, a value of 2 means the difference is between 5 and 9, etc. Edit distance between the social security numbers of the two records may also be utilized.

The results of the comparison of the various attributes obtained in step 410 may then be utilized to generate a false positive penalty in step 420. In one embodiment, the specific permutation of the set of results obtained from the comparison of the obtained at step 410 may be used to generate a false positive value. More specifically, in one embodiment, the combination of results obtained at step 410 may be used to access a data structure (e.g. index into a table, etc.) which may store a penalty value to be utilized based on that combination of results. In other words, the results of the comparisons may have an associated numeric value (e.g. "missing" for an attribute may have a value of 0, edit distance for an attribute may be a value of 1, etc.) and each of these numeric values may be used to index into a data structure to locate the false positive penalty associated with the particular permutation of results represented by those values. In one embodiment, a program (such as Python) may be used to generate data structures such as tables comprising false positive penalties for use with embodiments of the present invention.

In one particular embodiment, a four dimensional table may be utilized, with the first dimension of the table indexed by a value resulting from a combination of the result for the name comparisons and the result for the gender comparisons; the second dimension being the result of the edit distance comparisons between the date of birth attributes, the third dimension is the difference between the birth year of the two data records and the fourth dimension is the result of the edit distance comparisons between the SSNs of the two data records. For example, a certain false positive penalty corresponding to partial agreement on the name attribute between the two records, agreement of the gender attribute, an edit distance of one between the two date of birth attributes a difference of 20 or more on the year of birth and an edit distance of 3 between the two SSNs of the data records may correspond to entry (6, 2, 5, 4) in the table. FIG. 5 depicts one embodiment of a table for the various numeric values of a first dimension of such a table based upon a combination of the values of result for the name comparisons and the result for the gender comparisons as discussed above.

Returning to FIG. 4, once a false positive penalty has been determined at step 420 the overall weight previously determined for the two data records via a comparison of one or more of their various attributes may be adjusted using this false positive penalty. The determination of whether to link the two data records can then be based on the overall weight which has been adjusted by this false positive penalty (e.g. does the overall weight exceed a threshold, etc.). By tuning the false positive penalty imposed according to a variety of factors, which may include sample data collected from one or more data sources 34, 36, 38, the attributes used to generate the penalty, the comparisons used in conjunction with those attributes, etc. In fact, the set of attributes, and the comparisons utilized in conjunction with each of these attributes used to generate a false positive penalty may be almost infinitely tunable according to a wide variety of factors.

It may be helpful here to depict an example of various permutations of the results of the comparisons of various attributes which may cause a false positive penalty to be applied. FIG. 6 depicts one example of embodiments of permutations of comparisons results for certain attributes. In this example, the comparison results utilized are name, gender, SSN, date of birth (DOB), birth year difference and birth date edit distance. A false positive penalty may be imposed if there is a partial agreement between the name attribute of two data records (e.g. initial, phonetic or nickname match) but the gender attributes of the two records disagree; if the gender attributes disagree and the bate of birth attributes disagree; if the gender attributes disagree and the SSN attributes disagree; if there is a disagreement or partial agreement between the name attribute and the date of birth attributes disagree; if there is a disagreement or partial agreement between the name attribute and the SSN attributes disagree; if the is a greater than a 15 year difference in the birth year attributes of the two data records, and the edit distance between the two birth dates of the two data records is greater than 1.

It will be noted, in conjunction with the above discussions, that each of these values for the results of the comparisons of the various attributes may have a numerical value associated with it, and these values may be used to index a table comprising values for the false positive penalty to be imposed for any permutation of values from the results of the comparisons of attributes. Thus, for the above example, the values associated with each of the permutations listed in FIG. 6 may serve to index an entry in a table with a positive value for a false positive penalty while the numerical values associated with any other permutations of the results of the comparisons of these attributes may serve to index into a table with a zero value for the false positive penalty. In this manner, a false positive penalty may be imposed for the example permutations only.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

What is claimed is:

1. A method for association of data records, comprising: providing a system comprising an identity hub running an identity hub engine, the identity hub coupled to one or more external data sources through one or more networks, each external data source at a corresponding database;
   receiving a first data record and a second data record from the one or more external data sources at the identity hub;
   obtaining a first set of results, wherein each of the first set of results is a value generated based on a comparison between one of a first set of attributes from the first data record and the second data record, wherein the comparison between each of the first set of attributes is performed by the identity hub engine;
   determining a first overall weight for a comparison between the first data record and the second data record using the first set of results;
   generating a first false positive penalty based on the first set of results, wherein the first false positive penalty is associated with the comparison of the first data record and the second data record, and wherein each possible permutation of the first set of results corresponds to a different false positive penalty;
   adjusting the first overall weight to reduce a likelihood of incorrect linking of the first data record and second data record; and
   determining whether the first data record and the second data record should be linked based on the adjusted first overall weight.

2. The method of claim 1, wherein the first overall weight is determined using a second set of results wherein each of the second set of results is a value generated based on a comparison between one of a second set of attributes from the first data record and the second data record.

3. The method of claim 1, wherein the first false positive penalty is zero.

4. The method of claim 1, wherein the first set of attributes to use in determining the first false positive penalty was configured by a user.

5. The method of claim 1, further comprising:
- obtaining a second set of results, wherein each of the second set of results is based on a comparison between one of the first set of attributes from a third data record and a fourth data record, the second set of results differing from the first set of results, wherein obtaining the second set of results is performed by the identity hub engine;
- determining a second overall weight for a comparison between the third data record and the fourth data record using the second set of results;
- generating a second false positive penalty based on the second set of results wherein the second false positive penalty is associated with the comparison of the third data record and the fourth data record;
- adjusting the second overall weight to reduce the likelihood of the incorrect linking of the third data record and fourth data record; and
- determining whether the third data record and the fourth data record should be linked based on the adjusted second overall weight.

6. A computer readable storage media, comprising instructions translatable for implementing an identity hub engine on an identity hub the identity hub coupled to one or more external data sources through one or more networks, each external data source at a corresponding database the identity hub engine operable for:
- receiving a first data record and a second data record from the one or more external data sources at the identity hub;
- obtaining a first set of results, wherein each of the first set of results is a value generated based on a comparison between one of a first set of attributes from the first data record and the second data record, wherein the comparison between each of the first set of attributes is performed by the identity hub engine;
- determining a first overall weight for a comparison between the first data record and the second data record using the first set of results;
- generating a first false positive penalty based on the first set of results, wherein the first false positive penalty is associated with the comparison of the first data record and the second data record, and wherein each possible permutation of the first set of results corresponds to a different false positive penalty;
- adjusting the first overall weight to reduce a likelihood of incorrect linking of the first data record and second data record; and
- determining whether the first data record and the second data record should be linked based on the adjusted first overall weight.

7. The computer readable storage media of claim 6, wherein the first overall weight is determined using a second set of results wherein each of the second set of results is a value generated based on a comparison between one of a second set of attributes from the first data record and the second data record.

8. The computer readable storage media of claim 6, wherein the first false positive penalty is zero.

9. The computer readable storage media of claim 6, wherein the first set of attributes to use in determining the first false positive penalty was configured by a user.

10. The computer readable storage media of claim 6, wherein the identity hub engine is operable for:
- obtaining a second set of results, wherein each of the second set of results is based on a comparison between one of the first set of attributes from a third data record and a fourth data record, the second set of results differing from the first set of results, wherein obtaining the second set of results is performed by the identity hub engine;
- determining a second overall weight for a comparison between the third data record and the fourth data record using the second set of results;
- generating a second false positive penalty based on the second set of results wherein the second false positive penalty is associated with the comparison of the third data record and the fourth data record;
- adjusting the second overall weight to reduce the likelihood of the incorrect linking of the third data record and fourth data record; and
- determining whether the third data record and the fourth data record should be linked based on the adjusted second overall weight.

11. A system for the linking of data records, comprising:
- one or more data sources, each data source at a corresponding database; and
- an identify hub linked to the one or more data sources through one or more networks, wherein the identity hub comprising a computer readable medium including instructions operable for implementing an identity hub engine for:
  - receiving a first data record and a second data record from the one or more external data sources at the identity hub;
  - obtaining a first set of results, wherein each of the first set of results is a value generated based on a comparison between one of a first set of attributes from the first data record and the second data record, wherein the comparison between each of the first set of attributes is performed by the identity hub engine;
  - determining a first overall weight for a comparison between the first data record and the second data record using the first set of results;
  - generating a first false positive penalty based on the first set of results, wherein the first false positive penalty is associated with the comparison of the first data record and the second data record, and wherein each possible permutation of the first set of results corresponds to a different false positive penalty;
  - adjusting the first overall weight to reduce a likelihood of incorrect linking of the first data record and second data record; and
  - determining whether the first data record and the second data record should be linked based on the adjusted first overall weight.

12. The system of claim 11, wherein the first overall weight is determined using a second set of results wherein each of the second set of results is a value generated based on a comparison between one of a second set of attributes from the first data record and the second data record.

13. The system of claim 11, wherein the first false positive penalty is zero.

14. The system of claim 11, wherein the first set of attributes to use in determining the first false positive penalty was configured by a user.

15. The system of claim 11, wherein the identity hub engine is operable for:
- obtaining a second set of results, wherein each of the second set of results is based on a comparison between one of the first set of attributes from a third data record and a fourth data record, the second set of results differing from the first set of results, wherein obtaining the second set of results is performed by the identity hub engine;

determining a second overall weight for a comparison between the third data record and the fourth data record using the second set of results;
generating a second false positive penalty based on the second set of results wherein the second false positive penalty is associated with the comparison of the third data record and the fourth data record;
adjusting the second overall weight to reduce the likelihood of the incorrect linking of the third data record and fourth data record; and
determining whether the third data record and the fourth data record should be linked based on the adjusted second overall weight.

* * * * *